(12) United States Patent
Huang et al.

(10) Patent No.: US 9,993,168 B2
(45) Date of Patent: Jun. 12, 2018

(54) IMPLANTABLE PRESSURE MONITOR

(71) Applicant: University of Rochester, Rochester, NY (US)

(72) Inventors: Jason Haitao Huang, Temple, TX (US); Samantha Dayawansa, Temple, TX (US)

(73) Assignee: University of Rochester, Rochester, NY (US)

( * ) Notice: Subject to any disclaimer, the term of this patent is extended or adjusted under 35 U.S.C. 154(b) by 252 days.

(21) Appl. No.: 14/647,705

(22) PCT Filed: Nov. 25, 2013

(86) PCT No.: PCT/US2013/071757
§ 371 (c)(1),
(2) Date: May 27, 2015

(87) PCT Pub. No.: WO2014/085350
PCT Pub. Date: Jun. 5, 2014

(65) Prior Publication Data
US 2015/0289772 A1 Oct. 15, 2015

Related U.S. Application Data

(60) Provisional application No. 61/731,742, filed on Nov. 30, 2012.

(51) Int. Cl.
*A61B 5/02* (2006.01)
*A61B 5/022* (2006.01)
(Continued)

(52) U.S. Cl.
CPC ........ *A61B 5/02241* (2013.01); *A61B 5/0235* (2013.01); *A61B 5/02154* (2013.01);
(Continued)

(58) Field of Classification Search
CPC .............. A61B 5/02241; A61B 5/6884; A61B 5/02154; A61B 5/0235; A61B 5/6883; A61B 5/02255
See application file for complete search history.

(56) References Cited

U.S. PATENT DOCUMENTS

| | | | | |
|---|---|---|---|---|
| 5,353,800 A | * | 10/1994 | Pohndorf | A61B 5/0215 600/486 |
| 6,409,674 B1 | * | 6/2002 | Brockway | A61B 5/0028 600/486 |
| 2002/0041724 A1 | * | 4/2002 | Ronnekleiv | A61B 5/01 385/12 |

FOREIGN PATENT DOCUMENTS

JP 2010233883 A * 10/2010

* cited by examiner

*Primary Examiner* — Rex R Holmes
(74) *Attorney, Agent, or Firm* — Robert D. Gunderman, Jr.; Patent Technologies, LLC (57) ABSTRACT

There is provided an implantable pressure monitor having a fluid sack in contact with a body part of a patient where the fluid sack is retained to the body part by a pressure monitor housing that may have various attachment means. The fluid sack is filled with a liquid such as silicone oil. The pressure monitor housing has an opening that provides access to a fistula with a fluid valve that terminates through the fluid sack. A fiber optic pressure sensor is in contact with the liquid in the fluid sack by way of the fistula and fluid valve. In some embodiments of the present invention, an electronics module is incorporated with the implantable pressure monitor to provide telemetry, power, and the like.

19 Claims, 11 Drawing Sheets

(51) Int. Cl.
*A61B 5/0215* (2006.01)
*A61B 5/0235* (2006.01)
*A61B 5/00* (2006.01)
*A61B 5/0225* (2006.01)

(52) U.S. Cl.
CPC .......... *A61B 5/6883* (2013.01); *A61B 5/6884* (2013.01); *A61B 5/02255* (2013.01)

IMPLANTABLE PRESSURE MONITOR

This application claims priority to U.S. Patent Application Ser. No. 61/731,742 filed Nov. 30, 2012 entitled IMPLANTABLE PRESSURE MONITOR by Jason Haitao Huang and Samantha Dayawansa and to International Application Number PCT/US13/71757 filed Nov. 25, 2013 entitled IMPLANTABLE PRESSURE MONITOR by Jason Haitao Huang and Samantha Dayawansa, the entire disclosures of which are incorporated herein by reference.

TECHNICAL FIELD

The present invention relates generally to medical devices, and more particularly to an implantable pressure monitor that has a variety of applications such as blood pressure monitoring, aneurism monitoring, and the like.

BACKGROUND ART

The ability to monitor pressure in a living organism such as an animal or a human has numerous applications ranging from blood pressure monitoring to monitoring medical conditions such as aneurisms and the like. While monitoring blood pressure through the skin, for example, is known, the accuracy of such devices may be questionable. Targeted pressure monitoring of a medical condition such as an aneurism requires a precise and reliable device. Such a device should be non-invasive to the vessel itself to prevent problems associated with penetration of the blood vessel.

While monitoring of blood pressure or other pressure within a body is often done on a transitory basis, there are situations that require comprehensive continuous monitoring. For example, an aneurism may require continuous monitoring to ensure that it does not continue to grow in size and rupture. The ability to continuously monitor an aneurism, and provide the patient or a medical practitioner with real-time information related to their condition is something that has heretofore been unknown. Such continuous real-time monitoring allows immediate action to be taken in the event that the patient becomes at risk. Currently, aneurism monitoring involves regular surveillance imaging that requires a visit to a medical practitioner for each check of the condition of the aneurism. There is no real-time monitoring system that could provide pressure readouts on an instrument that could, for example, be worn on a patient's wrist, or provide the data to a remote monitoring device by way of a computer network, a wireless network, or the like.

It is thus an object of the present invention to provide an implantable pressure monitor that is non-invasive to the vessel or body part to which pressure is being monitored. It is another object of the present invention to provide an implantable pressure monitor that can provide data to a remote device such as a hospital monitor, smart phone, or other such electronic device. It is another object of the present invention to provide an implantable pressure monitor that provides real time status on medical conditions such as aneurisms. It is yet another object of the present invention to provide an implantable pressure monitor that provides real time blood pressure data. It is a further object of the present invention to provide an above skin blood pressure monitor. These and other objects of the present invention are not to be considered comprehensive or exhaustive, but rather, exemplary of objects that may be ascertained after reading this specification and claims in view of the accompanying drawings.

DISCLOSURE OF THE INVENTION

In accordance with the present invention, there is provided an implantable pressure monitor comprising a pressure monitor housing, a fluid sack retained by the pressure monitor housing, a liquid contained within the fluid sack, a fistula with a fluid valve that terminates through the fluid sack, an opening in the pressure monitor housing for access to the fistula, and a fiber optic pressure sensor in contact with the fluid by way of the fistula and fluid valve.

The foregoing paragraph has been provided by way of introduction, and is not intended to limit the scope of the invention as described by this specification, claims and the attached drawings.

BRIEF DESCRIPTION OF THE DRAWINGS

The invention will be described by reference to the following drawings, in which like numerals refer to like elements, and in which.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by this specification, claims and drawings attached hereto.

BEST MODE FOR CARRYING OUT THE INVENTION

The implantable pressure monitor of the present invention may have various embodiments, some of which are described herein, and others of which may be inferred from or otherwise envisioned based on the disclosure contained herein.

The implantable pressure monitor makes use of small changes in a body part (human or animal) to determine pressure. For example, a blood vessel experiences small "micro" movements as blood travels through the blood vessel. These movements can be correlated to blood pressure. In a similar way, pressure buildup in an organ or other body part can be detected by the implantable pressure monitor, providing an alert to a pending medical emergency. The implantable pressure monitor relies on the use of a fiber optic pressure sensor and a novel pressure sensing structure. The fiber optic pressure sensor may, in one embodiment of the present invention, be structured as a Fabry-Perot Interferometer such as the one disclosed in U.S. Pat. No. 7,684,657 to Donlagic et al. and entitled "Single Piece Fabry-Perot Optical Sensor And Method of Manufacturing Same", the entire disclosure of which is incorporated herein by reference in it's entirety. Other fiber optic pressure sensors may also be employed, and may, in some embodiments of the present invention, contain a moveable structure such as a diaphragm that changes position in relation to a reference (such as the end of the optical fiber) under varying pressure conditions to in turn provide pressure measurements through, for example, optical means. An example of a suitable fiber optic pressure sensor is the model FOP-F125 Pressure Sensor manufactured by FISO Technologies. Inc. of Quebec, Canada. The pressure sensing structure comprises a fluid filled sack that makes contact with the body part of which pressure is to be monitored. The fiber optic pressure sensor is in communication with the liquid contained in the fluid sack. This arrangement allows for sensing of small movements across a greater surface area, as opposed to what would essentially be a point source with the fiber optic pressure sensor alone. The fluid sack is in turn attached to the body part, for example a blood vessel like the aorta, by way of an accommodating and suitably shaped pressure monitor housing. The fiber optic pressure sensor may then be run outside the body to appropriate instrumentation to provide pressure readings, alerts, and the like. In some embodiments of the present invention, the fiber optic pressure sensor may terminate with an electronics module that is contained with the implantable pressure monitor. The electronics module in turn provides telemetry data to a hospital monitor, a smart phone, or other such electronic device that can provide pressure readings, alerts, alarms, and the like.

Several embodiments of the present invention will be described by way of the figures where FIGS. 1-7 describe a first embodiment, FIGS. 8-16 describe a second embodiment, and FIGS. 17-21 describe a third embodiment. The embodiments described and depicted herein are intended primarily for use with a blood vessel and related pressure measurements. One can envision after reading this disclosure an implantable pressure monitor that has a different shape and size to accommodate pressure monitoring of other anatomical parts such as, for example, internal organs. Such changes being considered within the spirit and broad scope of the present invention as described and depicted herein. In addition, an external, non-implantable pressure monitor using the fiber optic pressure sensor and the techniques described herein is also to be considered within the spirit and scope of the present invention. An output chart of such an embodiment of the present invention being depicted in FIG. 25.

Figure 1:
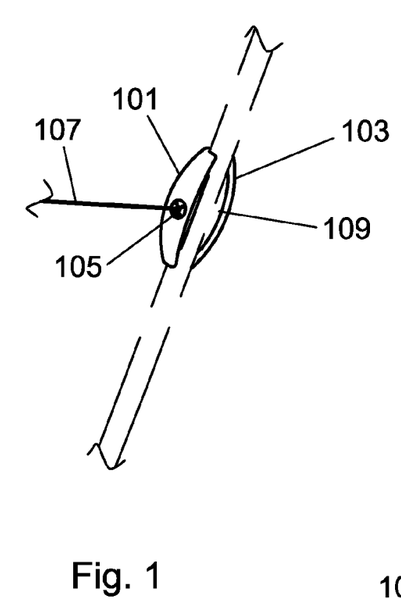
FIG. 1 is a perspective view of a wrap around pressure monitor on a vessel.

A first embodiment of the present invention, as depicted in FIGS. 1-7, attaches to a blood vessel by way of several retention parts that fold or hinge together. FIG. 1 is a perspective view of a wrap around pressure monitor on a vessel. A fluid sack 109 can be seen in contact with the blood vessel. The fluid suck 109 may be made from, for example, a metal foil, such as an aluminum foil, with suitable biocompatible coatings as necessary. The fluid sack 109 may also be made from a biocompatible cloth such as polyethylene terephthalate, also with suitable coatings as necessary. The fluid sack 109 contains a liquid such as, for example, silicone oil, that serves to transmit small movements of the blood vessel that correspond to pressure changes. Other liquids may also be employed such as a saline solution, water, or the like. Higher viscosity fluids are preferred due to their ability to transmit small pressure changes, but the present invention is not limited to such fluids. In fact, in some embodiments of the present invention, the fluid sack 109 may instead contain a gas, a gel, or the like. The fluid sack 109 may be of a shape conformal to the first retention part 101 and the second retention part 103. A fistula 105 having a fluid valve terminates through the fluid sack 109 so as to provide a liquid (or gas or gel) tight seal when the fiber optic pressure sensor 107 is placed through the fistula 105 and into the liquid, gas or gel contained in the fluid sack 109. The fistula 105 is made from a biocompatible material such as a stainless steel, a biocompatible plastic such as Polyethylene, Polysulfone, Polypropylene, or the like. A fistula, as used herein, refers to any opening, device, apparatus, seal, or structure that provides access to the inside of the fluid sack while keeping to contents of the fluid sack contained within. The fistula may, in some embodiments of the present invention, contain a fluid valve, seal, gasket, fitting, or similar structure to ensure a complete seal once the fiber optic pressure sensor is inserted into the fluid sack. The fistula may also simply be a pass through or via and may have suitable sealing material to ensure a leak free fit. The fistula 105 may be made by machining, casting, molding, or the like. An example of a suitable fistula can be seen in FIGS. 22-24. The fistula 105 seals to the fluid sack 109 using mechanical and sealant means, and also may contain a valve that may be a membrane or similar structure for sealing the liquid, gas or gel to the confines of the fluid sack 109 when the fiber optic pressure sensor 107 is inserted through the fistula 105 into the fluid sack 109. The fistula 105 passes through the pressure monitor housing by way of an opening in the first retention part 101 or the second retention part 103. To hold the fluid sack 109 against the blood vessel, a pressure monitor housing can be seen comprising a first retention part 101 and a second retention part 103. The first retention part 101 and the second retention part 103 may be made from a biocompatible material such as a stainless steel, a biocompatible plastic such as Polyethylene. Polysulfone. Polypropylene, or the like. The first retention part 101 and the second retention part 103 may be made by machining, casting, molding, or the like. Such an arrangement can be hinged, pinned, or otherwise connected so that the first retention part 101 and the second retention part 103 close around the fluid sack 109 in such a way that proper communication of small movements in the vessel are sent through the fluid contained in the fluid sack 109 to the fiber optic pressure sensor 107. The first retention part 101 and the second retention part 103 may, in some embodiments of the present invention, be one and the same (a single structure). For placement around vessels, the first retention part 101 and the second retention part 103 have a generally cylindrical inner cavity or surface to accommodate a vessel such as an artery or the like. In some embodiments of the present invention, the first retention part 101 and the second retention part 103 are of a similar shape and geometry and may be curved or otherwise shaped to conform to a vessel. In other embodiments of the present invention, the first retention part 101 and the second retention part 103 are of differing shape and geometry and may have areas where the fluid sack 109 is exposed or otherwise free from the first retention part 101 or the second retention part 103. The fiber optic pressure sensor 107 may, in one embodiment of the present invention, be structured as a Fabry-Perot Interferometer or otherwise contain a moveable structure such as a diaphragm that changes position in relation to a reference such as the end of the optical fiber under varying pressure conditions to in turn provide pressure measurements through, for example, optical means. A light source (not depicted) may be provided in optical communication with the fiber optic pressure sensor to provide an optical signal to the fiber optic pressure sensor, and a fiber optic receiver may be employed to receive the optical signal from the fiber optic pressure sensor. The received optical signal containing information that correlates with pressure readings, as seen, for example, in FIG. 25.

Figure 2:
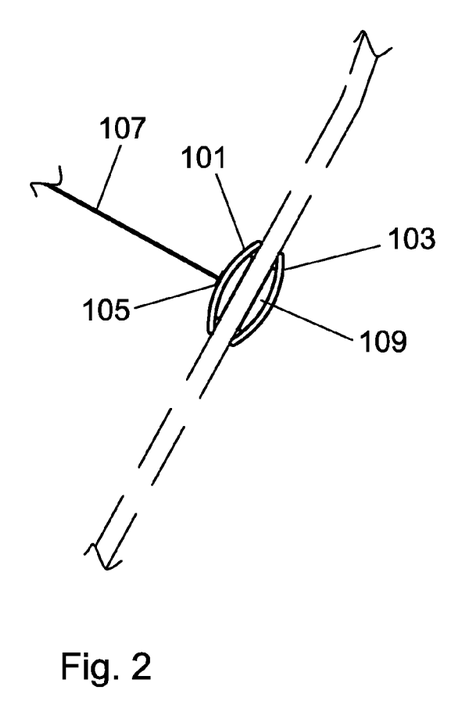
FIG. 2 is a plan view of the wrap around pressure monitor of FIG. 1.

The first retention part 101 and the second retention part 103 do not necessarily wrap completely around the blood vessel. FIG. 2 is a plan view of the wrap around pressure monitor of FIG. 1 showing a generally open side with the fluid sack 109.

Figure 3:
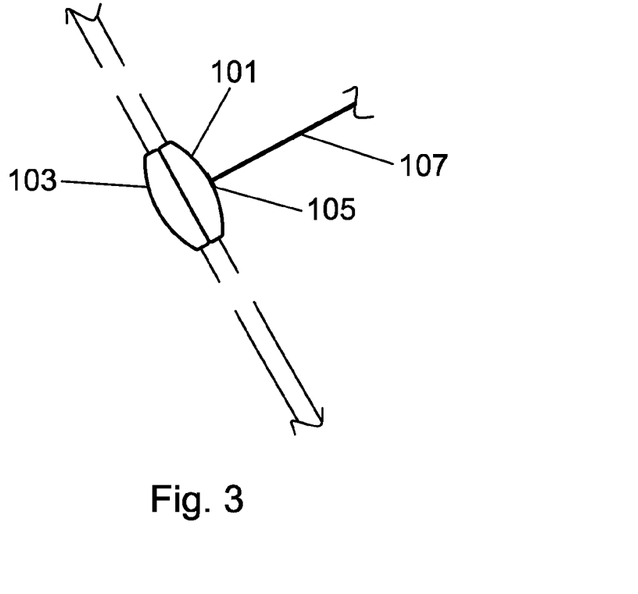
FIG. 3 is a rotated plan view of the wrap around pressure monitor of FIG. 1.
Figure 4:
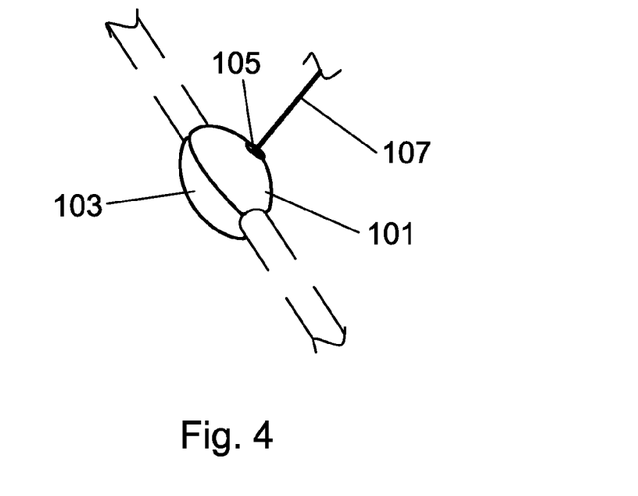
FIG. 4 is a rotated perspective view of the wrap around pressure monitor of FIG. 1.

FIG. 3 is a rotated plan view of the wrap around pressure monitor of the present invention and FIG. 4 is a rotated perspective view of the wrap around pressure monitor of the present invention. The fiber optic pressure sensor 807 can be seen exiting the fistula 105. The overall shape of the pressure monitor of the present invention may be, for example, a prolate spheroid or other similar geometry. Preferably, the shape of the pressure monitor should be devoid of sharp edges when implanted to avoid surgical complications. Various coatings may be applied to the pressure monitor such as drug eluting coatings and the like. In some embodiments of the present invention, the housing of the pressure monitor also serves to attach the pressure monitor to an anatomical part, either as a function of it's overall geometry, or as a function of features such as, for example, suture tabs, clamps, pins, and the like.

Figure 5:
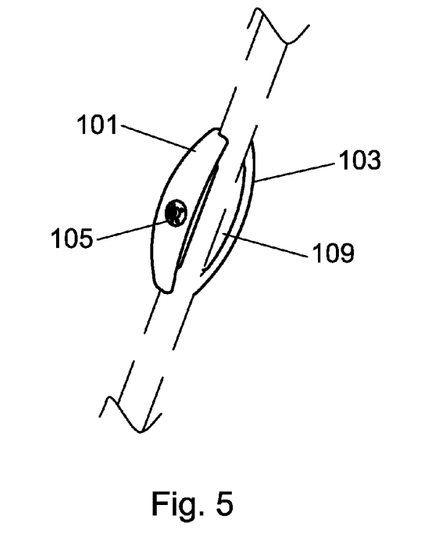
FIG. 5 is a perspective view of the wrap around pressure monitor of FIG. 1 without the fiber optic sensor.
Figure 6:
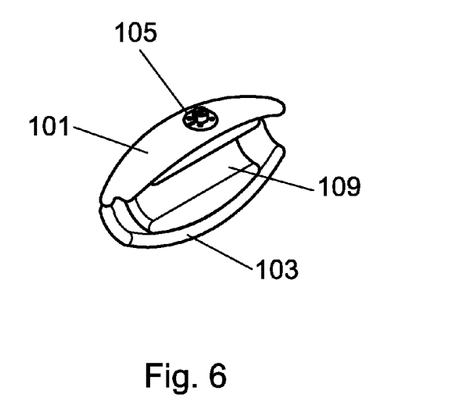
FIG. 6 is a perspective view of the wrap around pressure monitor of FIG. 1 in the open position.
Figure 7:
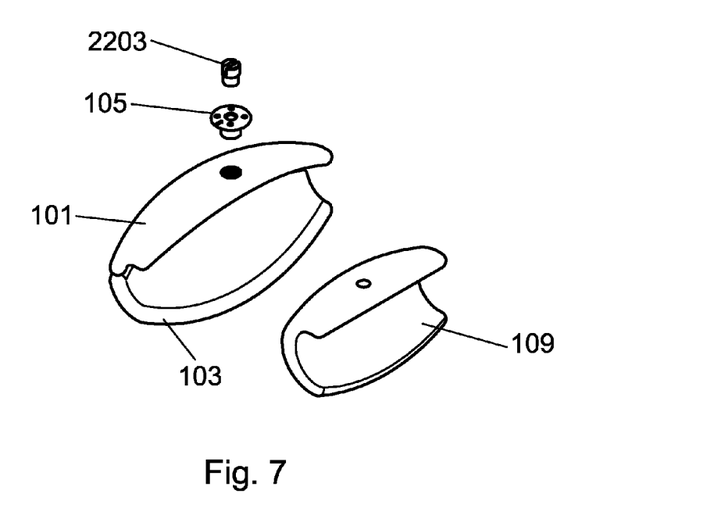
FIG. 7 is an exploded view of the wrap around pressure monitor of FIG. 1 in the open position.

FIG. 5 is a perspective view of the wrap around pressure monitor without the fiber optic sensor. FIG. 6 is a perspective view of the wrap around pressure monitor of FIG. 1 in the open position, and FIG. 7 is an exploded view of the wrap around pressure monitor in the open position showing clearly the fluid sack 109 within the pressure monitor housing. The embodiment depicted by way of FIGS. 1-7 may be useful, for example, with laboratory animals such as rats. The fiber optics will leave the body of the laboratory animal or human through a suitable fistula, and be connected to an appropriate interface that generates and reads the optical signals necessary to drive the fiber optic pressure sensor.

For applications that include use with humans, the overall pressure monitor should preferably be small in relation to the blood vessel or organ to which pressure is to be monitored. In addition, while in some clinical applications it may be acceptable to have the fiber optics leave the body through a suitable fistula, it oftentimes will be desirable to have electronics that provide the pressure data via telemetry to a receiving unit such as a hospital monitor, a smart phone, or other such electronic device that can provide pressure readings, alerts, alarms, and the like. These electronics may be integral with, or attached to, the pressure monitor, or may otherwise be in physical proximity to the pressure monitor of the present invention.

Figure 8:
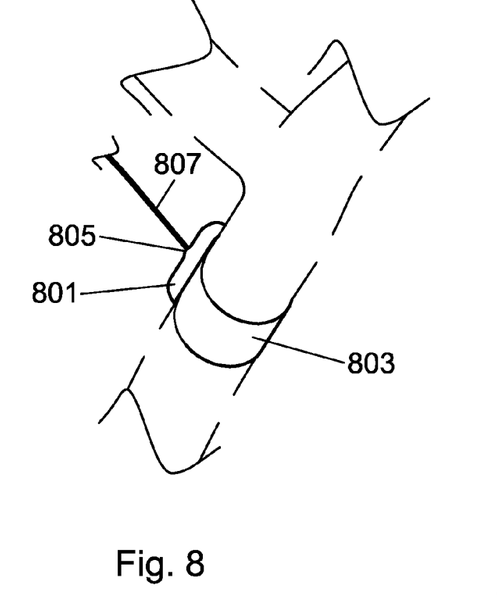
FIG. 8 is a perspective view of a strap based pressure monitor on a vessel.

FIGS. 8-16 describe a second embodiment of the implantable pressure monitor where the pressure monitor housing 801 is attached to the vessel, organ, or other anatomical part by way of a strap 803 as seen in the perspective view of FIG. 8. The strap 803 may be made from a suitable biocompatible material such as, for example, a biocompatible cloth such as, for example, polyethylene terephthalate. The strap 803 is an attachment structure for placing the pressure monitor on a body part. Other attachment structures such as hooks, pins, mesh, and the like may also be employed.

FIG. 8 is a perspective view of the strap based pressure monitor on a blood vessel. A fluid sack is contained within the pressure monitor housing 801 such that it makes contact with the blood vessel. The fluid sack can be seen in the cutaway view of FIG. 15 (see 1501). The fluid sack may be made from a metal foil, such as an aluminum foil, with suitable biocompatible coatings as necessary. The fluid sack may also be made from a biocompatible cloth such as polyethylene terephthalate, also with suitable coatings as necessary. The fluid sack contains a liquid such as, for example, silicone oil, that serves to transmit small movements of the blood vessel that correspond to pressure changes. Other liquids may also be employed such as a saline solution, water, or the like. Higher viscosity fluids are preferred due to their ability to transmit small pressure changes, but the present invention is not limited to such fluids. In fact, in some embodiments of the present invention, the fluid sack may instead contain a gas, a gel, or the like. A fistula 805 having a fluid valve terminates through the fluid sack so as to provide a liquid (or gas or gel) tight seal when the fiber optic pressure sensor 807 is placed through the fistula 805 and into the liquid, gas or gel contained in the fluid sack. The fistula 805 is made from a biocompatible material such as a stainless steel, a biocompatible plastic such as Polyethylene, Polysulfone, Polypropylene, or the like. A fistula, as used herein, refers to any opening, device, apparatus, seal, or structure that provides access to the inside of the fluid sack while keeping to contents of the fluid sack contained within. The fistula may, in some embodiments of the present invention, contain a fluid valve, seal, gasket, fitting, or similar structure to ensure a complete seal once the fiber optic pressure sensor is inserted into the fluid sack. The fistula may also simply be a pass through or via and may have suitable sealing material to ensure a leak free fit. The fistula 805 may be made by machining, casting, molding, or the like. An example of a suitable fistula can be seen in FIGS. 22-24. The fistula 805 seals to the fluid sack using mechanical and sealant means, and also may contain a valve that may be a membrane or similar structure for sealing the liquid, gas or gel to the confines of the fluid sack when the fiber optic pressure sensor 807 is inserted through the fistula 805 into the fluid sack. The fistula 805 passes through the pressure monitor housing by way of an opening. To hold the fluid sack against the blood vessel, a pressure monitor housing 801 can be seen. The pressure monitor housing 801 may be made from a biocompatible material such as a stainless steel, a biocompatible plastic such as Polyethylene, Polysulfone, Polypropylene, or the like. The pressure monitor housing 801 may be made by machining, casting, molding, or the like. The pressure monitor housing 801 encompasses the fluid sack in such a way that proper communication of small movements in the vessel are sent through the fluid contained in the fluid sack to the fiber optic pressure sensor 807. The fiber optic pressure sensor 807 may, in one embodiment of the present invention, be structured as a Fabry-Perot Interferometer or otherwise contain a moveable structure such as a diaphragm that changes position in relation to a reference such as the end of the optical fiber under varying pressure conditions to in turn provide pressure measurements through, for example, optical means. Other attributes and components from the pressure monitor disclosed by way of FIGS. 1-7 may also be incorporated with the embodiment depicted in FIGS. 8-16.

Figure 9:
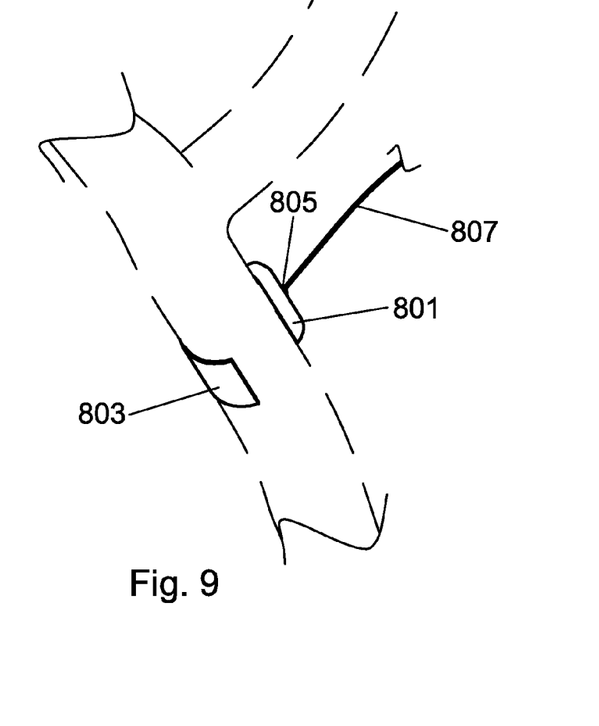
FIG. 9 is a rotated perspective view of the strap based pressure monitor of FIG. 8.

FIG. 9 is a rotated perspective view of the strap based pressure monitor. It should be noted that the strap 803 is shown as not completely encompassing the blood vessel or anatomical part The overall geometry of the strap 803 including it's length and width may vary based on the application, and in some embodiments of the present invention, the strap 803 may fully encompass the blood vessel or anatomical part.

Figure 10:
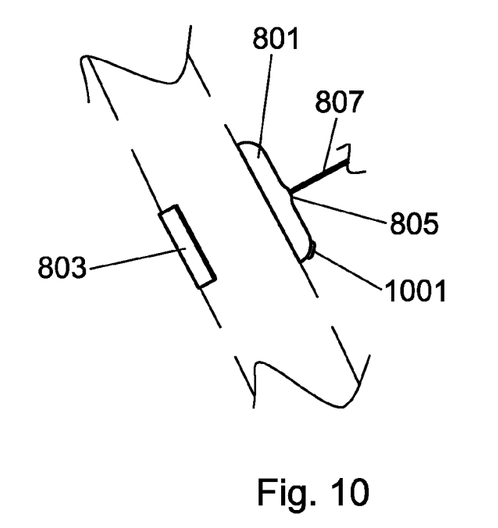
FIG. 10 is a rotated plan view of the strap based pressure monitor of FIG. 8.
Figure 11:
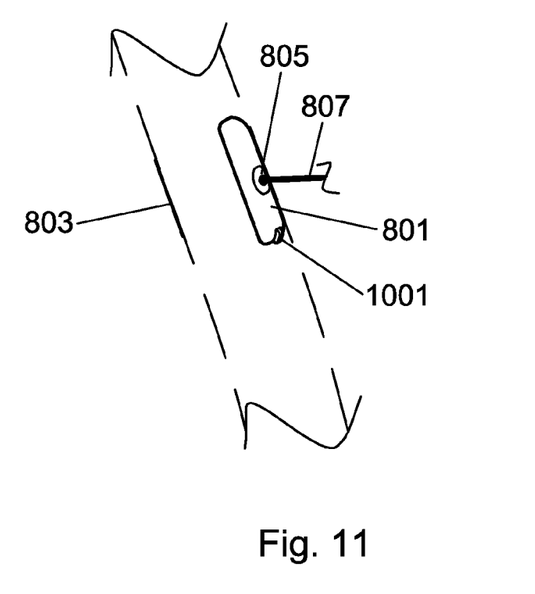
FIG. 11 is a top perspective view of the strap based pressure monitor of FIG. 8.
Figure 12:
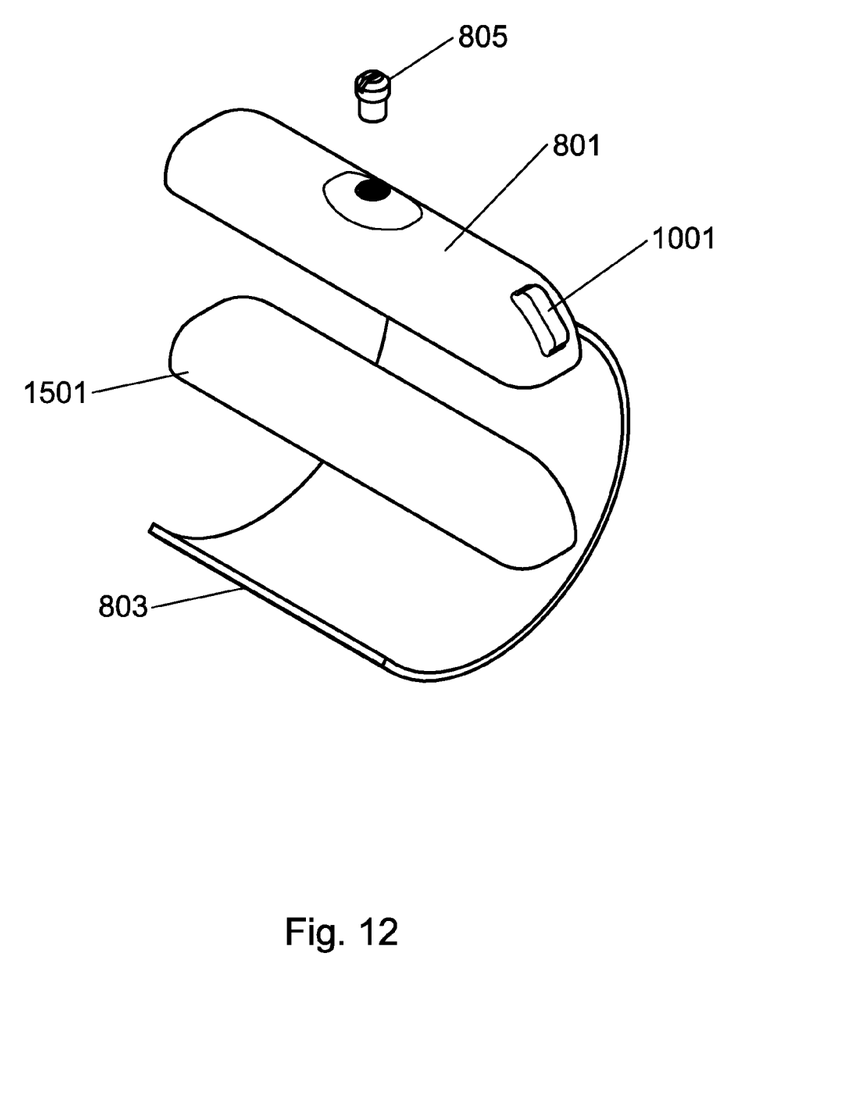
FIG. 12 is an exploded perspective view of the strap based pressure monitor of FIG. 8.
Figure 13:
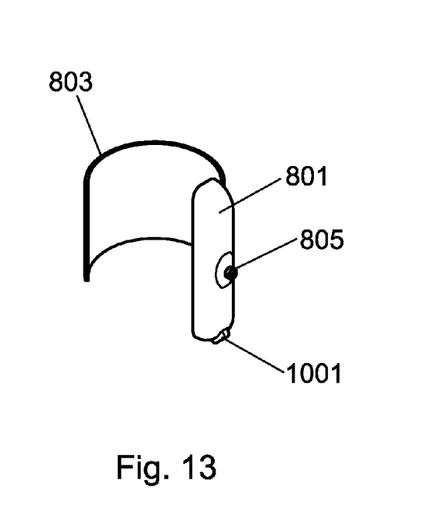
FIG. 13 is a perspective view of the strap based pressure monitor of FIG. 8 without the fiber optic pressure sensor.

FIG. 10 is a rotated plan view of the strap based pressure monitor. Shown in FIG. 10 is an electronics module 1001 that contains telemetry circuitry and power circuitry. The electronics module 1001 employs miniaturization techniques such as microelectronic design and packaging, hybrid circuit design and packaging, and the like. The electronics module 1001 contains an energy storage device that may be a battery, or may be a capacitor such as an ultracapacitor or the like. Suitable batteries include, but are not limited to, lithium ion implantable batteries or other microbatteries that are implantable. To charge the energy storage device, a charging coil may be employed that provides inductively coupled charging from an external source of electromagnetic radiation. Such an arrangement is described in United States Patent Application Publication US2009/0289595 A1 to Chen et al. and entitled "Wireless Charging Module and Electronic Apparatus", the entire disclosure of which is incorporated herein by reference. The charging coil (not shown) is made from a conductive material such as copper, and may be coiled or formed as a spiral. The conductive material may further be a wire, flat stock, printed conductive film, or the like. In addition, in some embodiments of the present invention, an energy harvesting device such as a MEMS device or a piezoelectric device to convert kinetic energy of the body into electrical energy is used to charge the energy storage device. The energy storage device contained within the electronics module 1001 provides power to the telemetry circuitry. The telemetry circuitry includes a fiber optic receiver with appropriate fiber optic terminations to receive the distal end of the fiber optic pressure sensor, which may, in some embodiments of the present invention, be contained within the pressure monitor housing 801. The telemetry circuitry contains both optical transmit and receive functionality as well as logic and related circuits to convert the optical signals from the fiber optic pressure sensor 807 into pressure data that is in turn transmitted from the electronics module 1001 to an external receiving unit such as a hospital monitor, smart phone, computer, or the like. The electronics module 1001 contains a radiofrequency transmitter capable of sending the pressure data, or may, in some embodiments of the present invention, contain circuitry capable of being interrogated by an external device and send the pressure data on demand. FIG. 11 is a top perspective view of the strap based pressure monitor. FIG. 12 is an exploded perspective view of the strap based pressure monitor depicting the fluid sack and related pressure monitor housing. FIG. 13 is a perspective view of the strap based pressure monitor without the fiber optic pressure sensor visible. As stated previously, the fiber optic pressure sensor may be terminated within the pressure monitor housing to the electronics module 1001 in some embodiments of the present invention.

Figure 14:
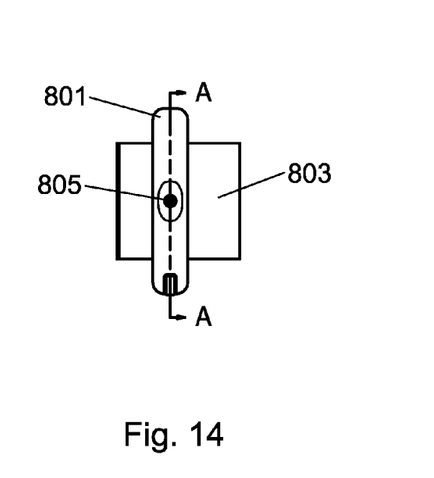
FIG. 14 is a plan view of the strap based pressure monitor of FIG. 8 without the fiber optic pressure sensor.
Figure 15:
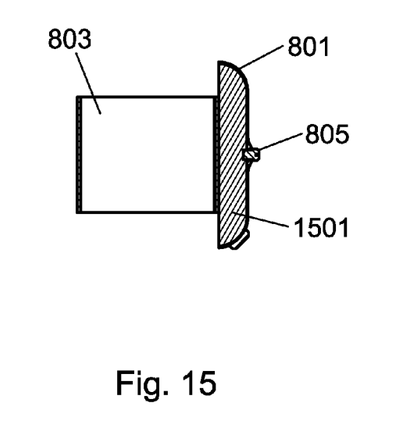
FIG. 15 is a plan view of the strap based pressure monitor cut along line A-A of FIG. 14.
Figure 16:
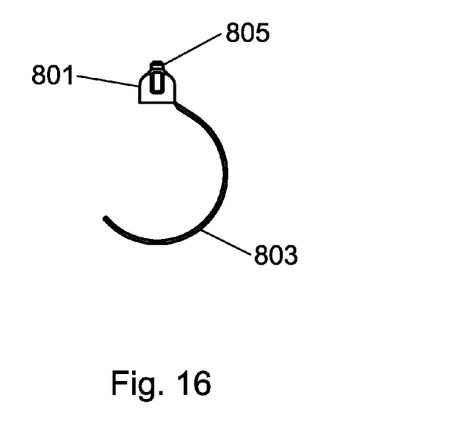
FIG. 16 is an end view of the strap based pressure monitor of FIG. 8 without the fiber optic sensor.

FIG. 14 is a plan view of the strap based pressure monitor without the fiber optic sensor visible and FIG. 15 is a plan view of the strap based pressure monitor cut along line A-A of FIG. 14. The internal fluid sack 1501 and internal fluid can be seen as the crosshatched area depicted. FIG. 16 is an end view of the strap based pressure monitor without the fiber optic sensor visible.

Figure 17:
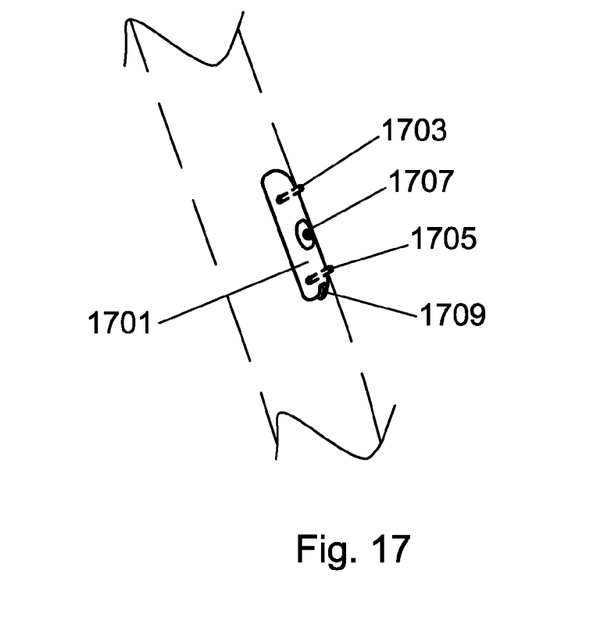
FIG. 17 is a perspective view of a suture tab pressure monitor on a vessel.

Similar to FIGS. 8-16 except for the mounting structure, FIGS. 17-21 describe a third embodiment of the implantable pressure monitor where the pressure monitor housing 1701 is attached to the vessel, organ, or other anatomical part by way of suture tabs such as the first suture tab 1703 and the second suture tab 1705 as seen in the perspective view of FIG. 17. The suture tabs are an attachment structure for placing the pressure monitor on a body part. Other attachment structures such as hooks, pins, mesh, and the like may also be employed. The suture tabs may be made from a biocompatible material such as a stainless steel, a biocompatible plastic such as Polyethylene, Polysulfone, Polypropylene, or the like. The suture tabs may be made by machining, casting, molding, or the like, and may be cast, molded, machined, or otherwise formed with the pressure monitor housing 1701. Other attributes and components from the pressure monitor disclosed by way of FIGS. 1-7 and FIGS. 8-16 may also be incorporated with the embodiment depicted in FIGS. 17-21.

FIG. 17 is a perspective view of a suture tab pressure monitor on a blood vessel. A fluid sack is contained within the pressure monitor housing 1701 such that it makes contact with the blood vessel. The fluid sack can be seen in the cutaway view of FIG. 21 (see 2101). The fluid sack may be made from a metal foil, such as an aluminum foil, with suitable biocompatible coatings as necessary. The fluid sack may also be made from a biocompatible cloth such as polyethylene terephthalate, also with suitable coatings as necessary. The fluid sack contains a liquid such as, for example, silicone oil, that serves to transmit small movements of the blood vessel that correspond to pressure changes. Other liquids may also be employed such as a saline solution, water, or the like. Higher viscosity fluids are preferred due to their ability to transmit small pressure changes, but the present invention is not limited to such fluids. In fact, in some embodiments of the present invention, the fluid sack may instead contain a gas, a gel, or the like. A fistula 1707 having a fluid valve terminates through the fluid sack so as to provide a liquid (or gas or gel) tight seal when the fiber optic pressure sensor (not shown) is placed through the fistula 1707 and into the liquid, gas or gel contained in the fluid sack. The fistula 1707 is made from a biocompatible material such as a stainless steel, a biocompatible plastic such as Polyethylene, Polysulfone, Polypropylene, or the like. A fistula, as used herein, refers to any opening, device, apparatus, seal, or structure that provides access to the inside of the fluid sack while keeping to contents of the fluid sack contained within. The fistula may, in some embodiments of the present invention, contain a fluid valve, seal, gasket, fitting, or similar structure to ensure a complete seal once the fiber optic pressure sensor is inserted into the fluid sack. The fistula may also simply be a pass through or via and may have suitable sealing material to ensure a leak free fit. The fistula 1707 may be made by machining, casting, molding, or the like. An example of a suitable fistula can be seen in FIGS. 22-24. The fistula 1707 seals to the fluid sack using mechanical and sealant means, and also may contain a valve that may be a membrane or similar structure for sealing the liquid, gas or gel to the confines of the fluid sack when the fiber optic pressure sensor is inserted through the fistula 1707 into the fluid sack. The fistula 1707 passes through the pressure monitor housing by way of an opening. To hold the fluid sack against the blood vessel, a pressure monitor housing 1701 can be seen. The pressure monitor housing 1701 may be made from a biocompatible material such as a stainless steel, a biocompatible plastic such as Polyethylene, Polysulfone, Polypropylene, or the like. The pressure monitor housing 1701 may be made by machining, casting, molding, or the like. The pressure monitor housing 1701 encompasses the fluid sack in such a way that proper communication of small movements in the vessel are sent through the fluid contained in the fluid sack to the fiber optic pressure sensor. The fiber optic pressure sensor may, in one embodiment of the present invention, be structured as a Fabry-Perot Interferometer or otherwise contain a moveable structure such as a diaphragm that changes position in relation to a reference such as the end of the optical fiber under varying pressure conditions to in turn provide pressure measurements through, for example, optical means.

Also depicted in FIG. 17 is an electronics module 1709 that contains telemetry circuitry and power circuitry. The electronics module 1709 employs miniaturization techniques such as microelectronic design and packaging, hybrid circuit design and packaging, and the like. The electronics module 1709 contains an energy storage device that may be a battery, or may be a capacitor such as an ultracapacitor or the like. Suitable batteries include, but are not limited to, lithium ion implantable batteries or other microbatteries that are implantable. To charge the energy storage device, a charging coil may be employed that provides inductively coupled charging from an external source of electromagnetic radiation. Such an arrangement is described in United States Patent Application Publication US2009/0289595 A1 to Chen et al. and entitled "Wireless Charging Module and Electronic Apparatus", the entire disclosure of which is incorporated herein by reference. The charging coil (not shown) is made from a conductive material such as copper, and may be coiled or formed as a spiral. The conductive material may further be a wire, flat stock, printed conductive film, or the like. In addition, in some embodiments of the present invention, an energy harvesting device such as a MEMS device or a piezoelectric device to convert kinetic energy of the body into electrical energy is used to charge the energy storage device. The energy storage device contained within the electronics module 1709 provides power to the telemetry circuitry. The telemetry circuitry includes a fiber optic receiver with appropriate fiber optic terminations to receive the distal end of the fiber optic pressure sensor, which may, in some embodiments of the present invention, be contained within the pressure monitor housing 1701. The telemetry circuitry contains both optical transmit and receive functionality as well as logic and related circuits to convert the optical signals from the fiber optic pressure sensor into pressure data that is in turn transmitted from the electronics module 1709 to an external receiving unit such as a hospital monitor, smart phone, computer, or the like. The electronics module 1709 contains a radiofrequency transmitter capable of sending the pressure data, or may, in some embodiments of the present invention, contain circuitry capable of being interrogated by an external device and send the pressure data on demand.

Figure 18:
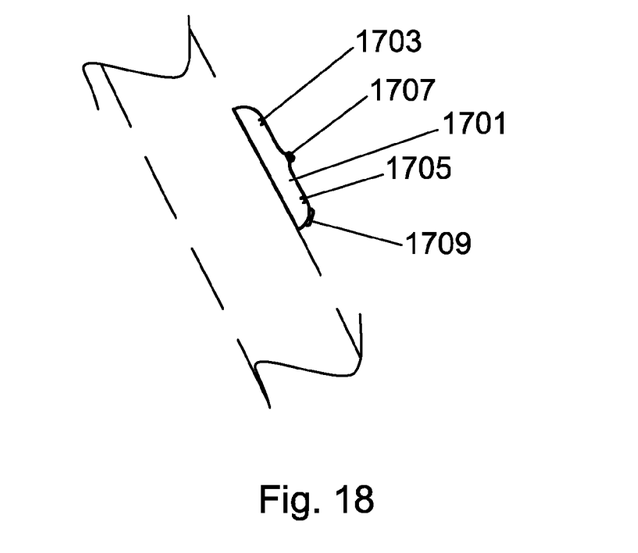
FIG. 18 is a side plan view of the suture tab pressure monitor of FIG. 17.
Figure 19:
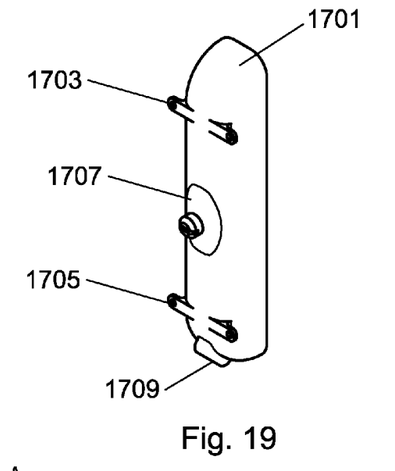
FIG. 19 is a perspective view of the suture tab pressure monitor of FIG. 17.
Figure 20:
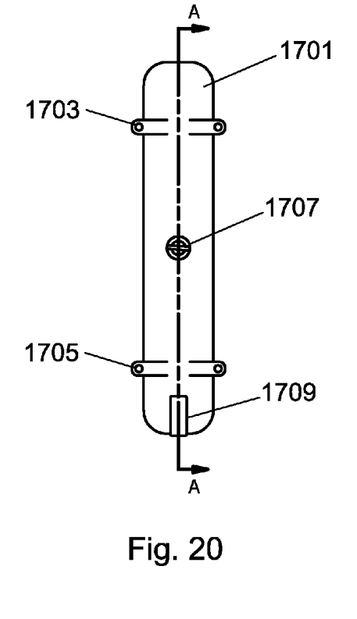
FIG. 20 is a top plan view of the suture tab pressure monitor of FIG. 17.
Figure 21:
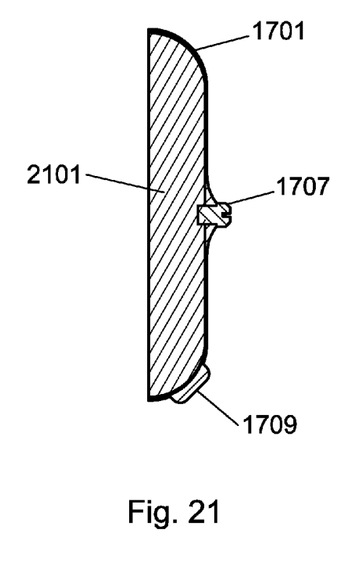
FIG. 21 is a plan view of the suture tab pressure monitor cut along line A-A of FIG. 20.

FIG. 18 is a side plan view of the suture tab pressure monitor in use on a blood vessel. FIG. 19 is a perspective view of the suture tab pressure monitor showing the suture tabs used to hold the pressure monitor in place. FIG. 20 is a top plan view of the suture tab pressure monitor. FIG. 21 is a plan view of the suture tab pressure monitor cut along line A-A of FIG. 20 showing the fluid sack 2101 and internal fluid by way of the cross hatched area.

Figure 22:
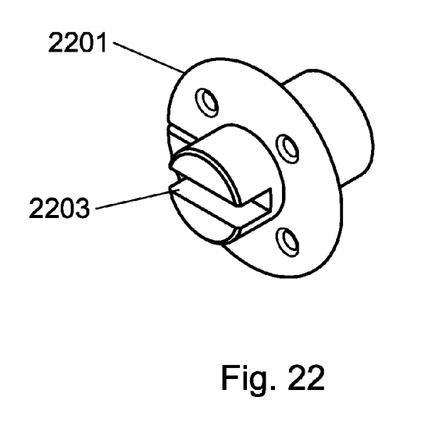
FIG. 22 is a perspective view of a fistula of the present invention.
Figure 23:
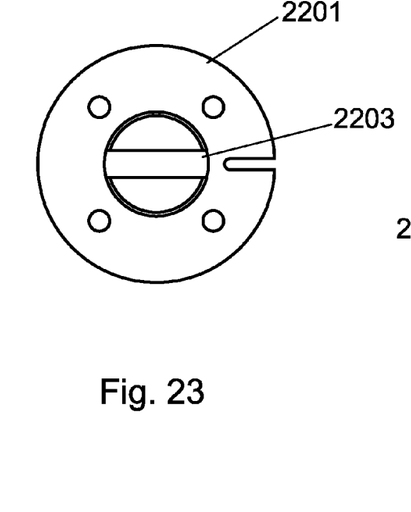
FIG. 23 is a side plan view of a fistula of the present invention.
Figure 24:
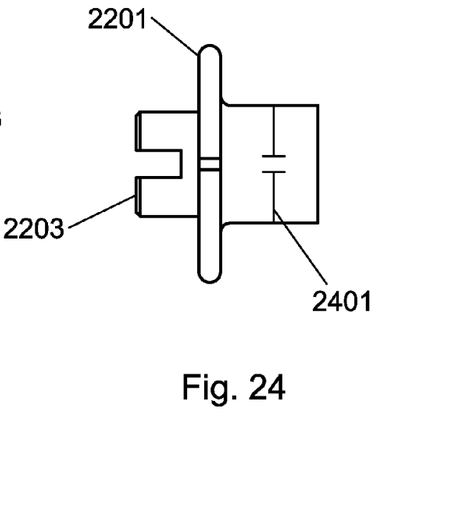
FIG. 24 is a top plan view of a fistula of the present invention.

FIGS. 22-24 depict an exemplary fistula of the present invention. FIG. 22 is a perspective view of a fistula 2201. The fiber optic pressure sensor port 2203 can be seen. FIG. 23 is a side plan view of the fistula 2201 where a valve 2401 can be seen. The valve 2401 provides a liquid (or gas or gel) tight seal when the fiber optic pressure sensor is placed through the fistula and into the liquid, gas or gel contained in the fluid sack. The valve 2401 may be made from a membrane, a flexible silicone rubber, a mechanical fixture, or the like. The fistula 2201 is made from a biocompatible material such as a stainless steel, a biocompatible plastic such as Polyethylene, Polysulfone, Polypropylene, or the like. A fistula, as used herein, refers to any opening, device, apparatus, seal, or structure that provides access to the inside of the fluid sack while keeping to contents of the fluid sack contained within. The fistula may, in some embodiments of the present invention, contain a fluid valve, seal, gasket, fitting, or similar structure to ensure a complete seal once the fiber optic pressure sensor is inserted into the fluid sack. The fistula may also simply be a pass through or via and may have suitable sealing material to ensure a leak free fit. The fistula 2201 may be made by machining, casting, molding, or the like. The fiber optic pressure sensor port 2203 is depicted as a slot, but other embodiments of the present invention use varying geometries. In addition, the overall geometry of the fistula 2201 may vary from one embodiment to another. FIG. 24 is a top plan view of a fistula of the present invention.

Figure 25:
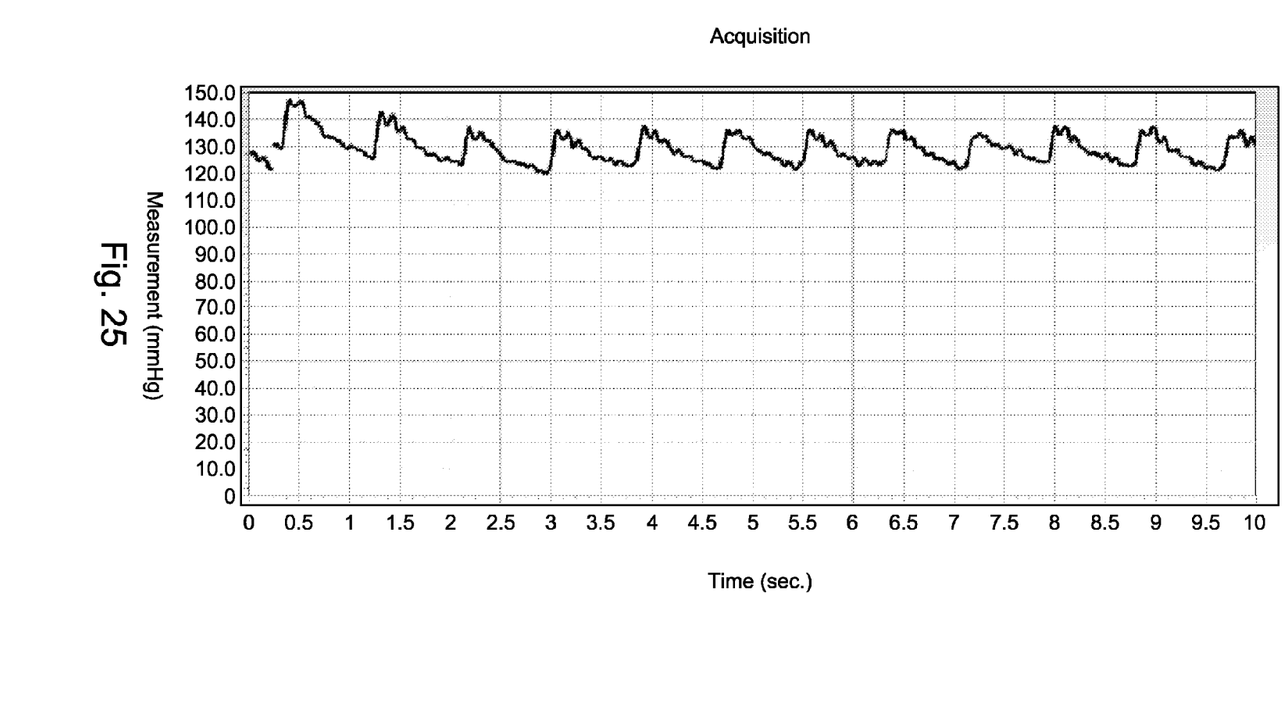
FIG. 25 is a chart recording of micro movements of a patient's skin over the external carotid artery expressed as pressure vs. time.

FIG. 25 is a chart recording of micro movements of a patient's skin over the external carotid artery expressed as pressure vs. time. An above the skin version of the present invention contains the fiber optic pressure sensor in direct contact with the skin above a monitoring point such as the external carotid artery. Small movements of the skin can be directly correlated with pressure changes. The chart in FIG. 25, for example, depicts pressure changes in the range of 120 to 149 millimeters of mercury. The chart in FIG. 25 has a y-axis range from zero to 150.0. The scale is thus millimeters of mercury (mm. Hg). In some embodiments of the present invention, a fluid sack, such as the fluid sack previously described herein, is placed between the patient's skin and the fiber optic pressure sensor. Such an arrangement may be packaged in a suitable housing, and may contain electronics to transmit the pressure information to a receiving device for subsequent display or storage. The receiving device may be worn on the patient's wrist, or it may be a device that is connected to a computer network for subsequent data transmission, display, and storage.

To use the implantable pressure monitor, the fluid sack is placed against the blood vessel, organ, or anatomical part of interest. The pressure monitor housing containing the fluid sack is then attached by way of a strap, sutures, retention parts, or the like. The fiber optic pressure sensor is then either guided outside the body or terminated with the electronics module.

While the pressure monitor described herein is suitable for implantation, the use of the novel pressure sensing structure (fluid sack and related fixtures) and fiber optic pressure sensor in above skin applications is also to be considered within the spirit and broad scope of the present invention.

It is, therefore, apparent that there has been provided, in accordance with the various objects of the present invention, an implantable pressure monitor.

While the various objects of this invention have been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of this specification, claims, and drawings appended herein.

What is claimed is:

1. An implantable pressure monitor comprising:
a pressure monitor housing having a first open end and a second open end to allow for longitudinal placement around the exterior of a blood vessel in situ;
a fluid sack retained by the pressure monitor housing and positioned with the pressure monitor housing to allow contact with the exterior of the blood vessel when implanted;
a liquid contained within the fluid sack;
a fistula with a fluid valve that terminates through the fluid sack;
an opening in the pressure monitor housing for access to the fistula; and
a fiber optic pressure sensor in communication with the liquid by way of the fistula and fluid valve.

2. The implantable pressure monitor of claim 1, wherein the pressure monitor housing comprises a first retention part and a second retention part mechanically joined together.

3. The implantable pressure monitor of claim 1, wherein the pressure sensor is a Fabry-Perot Interferometer.

4. The implantable pressure monitor of claim 1, further comprising an electronics module coupled to the pressure sensor.

5. The implantable pressure monitor of claim 1, wherein the liquid contained within the fluid sack is a high viscosity liquid.

6. The implantable pressure monitor of claim 1, wherein the pressure monitor housing has the general shape of a prolate spheroid.

7. A pressure monitor comprising:
a pressure monitor housing having a first open end and a second open end to allow for longitudinal placement around the exterior of a blood vessel in situ;
a fluid sack retained by the pressure monitor housing and positioned with the pressure monitor housing to allow contact with the exterior of the blood vessel when implanted;
an opening in the pressure monitor housing to allow the fluid sack to make contact with the blood vessel when implanted;
a liquid contained within the fluid sack;
a fistula with a fluid valve that terminates through the fluid sack; and
a fiber optic pressure sensor in communication with the liquid by way of the fistula and fluid valve.

8. The pressure monitor of claim 7, further comprising an electronics module coupled to the pressure sensor.

9. The pressure monitor of claim 7, wherein the pressure sensor is a Fabry-Perot Interferometer.

10. The pressure monitor of claim 7, further comprising telemetry circuitry.

11. The pressure monitor of claim 7, wherein the liquid contained within the fluid sack is a high viscosity liquid.

12. An implantable pressure monitor comprising:
a pressure monitor housing having a first open end and a second open end to allow for longitudinal placement around the exterior of a blood vessel in situ;
an attachment structure mechanically affixed to the pressure monitor housing and capable of attaching and retaining the implantable pressure monitor to an exterior of a blood vessel;
a fluid sack retained by the pressure monitor housing and positioned with the pressure monitor housing to allow direct physical contact of the fluid sack with the exterior of the blood vessel when implanted;
a liquid contained within the fluid sack;
a fistula with a fluid valve that terminates through the fluid sack;
an opening in the pressure monitor housing for access to the fistula; and
a fiber optic pressure sensor in communication with the liquid by way of the fistula and fluid valve.

13. The implantable pressure monitor of claim 12, wherein the pressure sensor is a Fabry-Perot Interferometer.

14. The implantable pressure monitor of claim 12, further comprising an electronics module coupled to the pressure sensor.

15. The implantable pressure monitor of claim 12, wherein the liquid contained within the fluid sack is a high viscosity liquid.

16. The implantable pressure monitor of claim 12, wherein the attachment structure is a strap.

17. The implantable pressure monitor of claim 12, wherein the attachment structure is a suture tab.

18. The implantable pressure monitor of claim 12, wherein the attachment structure is a plurality of suture tabs.

19. The implantable pressure monitor of claim 12, wherein the pressure monitor housing is open on one side to allow the fluid sack to contact a body part.

* * * * *